United States Patent [19]

Eibl et al.

[11] Patent Number: 4,814,277

[45] Date of Patent: Mar. 21, 1989

[54] METHOD OF INACTIVATING REPRODUCTIVE FILTERABLE PATHOGENS

[75] Inventors: Johann Eibl; Yendra Linnau, both of Vienna, Austria

[73] Assignee: Immuno Aktiengesellschaft fur chemisch-medizinische Produkte, Vienna, Austria

[21] Appl. No.: 48,774

[22] Filed: May 12, 1987

[30] Foreign Application Priority Data

May 30, 1986 [AT] Austria ................................. 1457/86

[51] Int. Cl.⁴ .............................................. C07K 3/00
[52] U.S. Cl. .................................... 435/269; 435/272
[58] Field of Search ........................................ 435/269

[56] References Cited

U.S. PATENT DOCUMENTS 2,065,196 12/1936 Parfentjev ............................ 435/269
4,312,949 1/1982 Ahrens ................................. 435/269

FOREIGN PATENT DOCUMENTS 0035204 2/1981 European Pat. Off. .
0053338 11/1981 European Pat. Off. .
0077870 2/1982 European Pat. Off. .
0139975 8/1984 European Pat. Off. .
58-040532 4/1983 Japan .
WO82/03871 11/1982 PCT Int'l Appl. .
WO83/04371 12/1983 PCT Int'l Appl. .

*Primary Examiner*—Sam Rosen
*Attorney, Agent, or Firm*—Burns, Doane, Swecker & Mathis

[57] ABSTRACT

A method of inactivating reproductive filterable pathogens in immunoglobulin-G-containing blood fractions to be applied therapeutically or prophylactically. In order to preserve full activity of the blood products and to completely inactivate pathogenic viruses, an aqueous solution of an immunoglobulin-G-containing fraction obtained from human blood is treated with neutral hydrolases at a temperature of 4° to 50° C. and at a pH of 5.5 to 9.5.

8 Claims, No Drawings

METHOD OF INACTIVATING REPRODUCTIVE FILTERABLE PATHOGENS

The invention relates to a method of inactivating reproductive filterable pathogens in immunoglobulin-G-containing blood fractions to be applied therapeutically or prophylactically, optionally by applying an elevated temperature.

There is available comprehensive literature dealing with the inactivation of reproductive filterable pathogens in blood products. The various methods, i.a., comprise:

heating the blood products in aqueous solutions, optionally by adding stabilizing substances,
treating the blood products with organic solvents,
heating the blood products in dry state.

With these methods of inactivation, there is the desire to neutralize the potential infectiousness of the preparations, yet to largerly maintain their biologic activities. So far, this aim has not been reached to a satisfactory degree. Primarily, these methods are not applicable, or only poorly applicable, with solutions containing immunoglobulin.

In detail, the following documents may be mentioned as part of the prior art:

European patent application No. 0,139,975 relates to a method of pasteurizing human plasma, wherein a plasma solution is heated to a temperature of up to 70° C. in the presence of calcium ions and of sucrose.

European Pat. No. 0,053,338 describes a process of inactivating hepatitis viruses in preparations containing Factors IX and X, wherein heating of the aqueous solution of a blood preparation is effected at temperatures of up to 100° C. in the presence of calcium ions and, if desired, an amino acid and/or a saccharide or sugar alcohol.

In European patent application No. 0,035,204, a method for inactivating aqueous protein solutions that may contain Factor VIII, fibronectin, globulin, fibrinogen and other proteins is described, wherein the composition is mixed with a polyol and the mixture is heated to a temperature of 60° to 75° C.

In European patent application No. 0,077,870, an inactivating process is disclosed, in which an aqueous solution containing Factor VIII is heated to 50° to 80° C., together with amino acids, monosaccharides, oligosaccharides, sugar alcohols and hydrocarbon carboxylic acids or hydroxyhydrocarbon carboxylic acids having 3 to 10 carbon atoms.

In PCT application No. WO 83/04371, a method of inactivating hepatitis virus is described, wherein a preparation containing the virus is treated with a halohydrocarbon, in particular chloroform, at a temperature of 4° to 40° C.

Published PCT application No. WO 82/03871 describes a method for treating blood clotting enzyme compositions, wherein the latter are heated in dry condition, optionally upon addition of stabilizing agents, such as, e.g., amino acids and/or sugars, in order to inactivate infectious viruses contained therein; as dry state, such having less than 5% by weight (0.05) of water is defined.

In Japanese document No. 51-118825, a process for thermally stabilizing IgA (immunoglobulin A) and IgM (immunoglobulin M) is described, wherein hepatitis viruses are to be activated by thermal treatment of the immunoglobulin-containing solution at 60° C. in the presence of neutral amino acids and monosaccharides.

Finally, it is referred to European patent application No. 0,122,909, in which a method for the preparation of an intravenously administrable fraction containing immunoglobulin G is described. With this method, an immunoglobulin-G-containing fraction is treated with pankreas enzymes bound to water insoluble carrier material with a view to eliminating impurities causing vasoactive or leucopenic effects and, thus, incompatibility reactions. Nothing is said in that document as to the inactivating effects with regard to pathogens.

Although a great number of inactivation methods have been proposed, as is apparent from the prior art mentioned, all these methods have certain disadvantages, such as non-satisfactory yields and/or reduction of the biologic efficacy or non complete inactivation of all the viruses in question; or they are not applicable to immunoglobulin-G-containing preparations in liquid phase without having one of the disadvantages pointed out.

The invention aims at avoiding these disadvantages and difficulties and has as its object to provide an inactivation method for immunoglobulin-G-containing preparations, which is safe in that pathogenic viruses will no longer be present when applying the same, the activities of the blood products being fully preserved.

With a method of the initially defined kind, the invention, by which this object is achieved, consists in that an aqueous solution of an immunoglobulin-G-containing fraction obtained from human blood is treated with neutral hydrolases at a temperature of 4° to 50° C. and at a pH of 5.5 to 9.5.

As neutral hydrolases, one or several enzymes of the group of peptide hydrolases, such as trypsin, chymotrypsin, pepsin, carboxypeptidases, may be used.

When applying the invention to prepare immunoglobulin G preparations, it is preferred to separate the enzyme(s) from the solution after inactivation and to subject the treated product to a further purification and concentration.

According to one embodiment of the invention, the aqueous solution of the immunoglobulin-G-containing fraction is treated with a soluble hydrolase at a pH of 6.0 to 8.0, preferably 7.0±0.4.

According to another embodiment of the invention, the aqueous solution of the immunoglobulin-G-containing fraction is treated with a (immobilized) neutral hydrolase bound to water insoluble carrier material at a pH of 5.5 to 8.5.

According to an advantageous embodiment, the treatment of the immunoglobulin-G-containing fraction is carried out at elevated temperature for a period of 1 hour to 36 days.

The protein concentration of the immunoglobulin-G-containing fraction may be 0.1 to 18% by weight.

Among the reproductive filterable pathogens to be reliably inactivated by the method of the invention, hepatitis virus or HTLV-III/LAV virus (human T lymphotropic virus) are to be emphasized.

Since the necessary assays on hepatitis virus inactivation in blood products cannot be performed directly in man and chimpanzees are available in an insufficient number only, the assessment of the inactivation efficacy according to the invention has been effected by the aid of model viruses.

The activation method according to the invention as well as the preparation of an immunoglobulin-G-containing preparation by applying this method, the effects attained and the superiority of this method over known methods will be explained in more detail in the following examples and tables.

EXAMPLE 1

(a) Preparation of an immunoglobulin-G-containing fraction:

Human blood plasma is admixed with 8% ethanol at a pH of 7.2 and a temperature of −2° C. Upon separation of the precipitate, the ethanol concentration is raised to 25%, the temperature simultaneously being lowered to −6° C. The precipitates, which contains immunoglobulin G, is further purified by extraction with phosphate acetate buffer and subsequently is admixed with 12% ethanol at a pH of 5.4 and a temperature of −2° C. The precipitate is discarded. The ethanol concentration of the supernatant is raised to 25% at a pH of 7.2 and a temperature of −8° C. The pasty immunoglobulin precipitated is collected and the ethanol is removed by dialysis, freeze-drying or ultrafiltration.

The immunoglobulin-G-containing fraction is adjusted to a protein content of 10% and is sterilized by filtration.

(b) Inactivation of vaccinia virus with immobilized trypsin:

The immobilized trypsin used in this example was prepared in the following way:

1 liter sepharose 4 B gel (Pharmacia), upon washing with 4 liter distilled water, was mixed with 200 g bromcyanogen dissolved in 100 ml acetonitril at a pH of 11.0. The reaction mixture was cooled by an ice bath. Upon elimination of the liquid phase, the gel was mixed with 800 mg trypsin (Sigma) dissolved in 1 liter 0.2 molar $NaHCO_3$. The nonbound trypsin was separated by filtration from the trypsin bound to the gel.

After having mixed the immobilized trypsin with 1 liter of a 1 molar glycine solution, it was thoroughly washed free of protein with 0.2 molar $NaHCO_3$ solution. Finally, it was suspended in 1 Liter 0.9% NaCl solution—it is ready for use to be incubated with an immunoglobulin fraction.

10 ml of the immunoglobulin solution obtained according to lit. (a) were mixed with 1 ml of the immobilized trypsin described above and with 0.5 ml of a vaccinia virus suspension (vaccinia virus, ATCC VR-862, virus strain Elstree, Amercian Type Culture Collection) and were treated under sterile conditions at 37° C. by stirring.

A comparative solution, containing 10 ml of the immunoglobulin solution according to (a), 1 ml immobilized trypsin and 0.5 ml virus-free medium, was prepared to determine the IgG monomers and biologic activity and was treated in the same way as the virus containing solution (equal temperature, equal period of stirring).

Samples of the virus containing solution were taken and the virus titer was determined at the beginning and after various time intervals, i.e., after 24 h, 48 h and 75 h. This was effected in the following manner:

The virus containing solution was diluted in series with isotonic saline solution at a ratio of 1:10. The titer of the virus was determined by assessment of the cytopathic effect on sensitive vero cells in the microtiter plate. The results have been expressed as logarithm $TCID_{50}$ upon statistic treatment of the evaluation according to the formula by Reed and Muench (Reed J. L. and H. Muench; Amer. J. Hyg. 27, 493–497, (1938).

The virus titers obtained may be taken from Table 1, from which it is apparent that the virus titer present at the beginning of the assay of 2.6 fell to 1.0 after 24 h and to less than 1.0 after 48 h.

(c) Determination of the biologic activity, i.e., of the content of tetanus antibodies in IU/ml and of the portion of IgG monomers in virus-free samples:

The determination of tetanus antibodies is based on that a determined amount of tetanus toxin is mixed with different amounts of tetanus antitoxin-containing samples and injected in mice after previous incubation. The International Units/ml are evaluated on grounds of the occurring death rates as compared to the WHO standard (Europ. Pharmakopoeia, 2nd Ed., Part. II-2, pp. 91-91-3, 1981).

The determination of the content of IgG monomers was effected by means of HPLC (high performance liquid chromatography) by subjecting the IgG-containing comparative solution to HPLC analysis. As separation column, a Bio Sil TSK 250 column, 600×7.5 mm, for a molecular weight range of 1,000 to 300,000 was used. As eluant, a sodium dehydrogen phosphate-sodium sulfate buffer, pH 6.8, was used. As monomer content, the peak with values for Ve/Vo of 1.28–1.67 was used (T. Tomono et al., Analytical Biochemistry, 123: 394–401, 1982).

EXAMPLE 2

Inactivation of Sindbis virus with immobilized trypsin 10 ml of an immunoglobulin-G-containing solution prepared in the same manner as in Example 1, were mixed with 1 ml immobilized trypsin and 0.5 Ml of a Sindbis virus suspension (ATCC VR-68, virus strain AR 339, American Type Culture Collection) and treated under sterile conditions at 37° C. by stirring. As comparative solution for activity assessment, the same solution as in Example 1 served.

Samples were taken at the beginning and after various time intervals and the virus titer was determined.

The results may be taken from Table 2: Departing from 4.5, the Sindbis virus titer had fallen to 1.9 by 2.6 log steps after 75 h. The contents of tetanus antibodies and of IgG monomers correspond to the values indicated in Table 1.

EXAMPLE 3

Inactivation of HTLV-III$_B$ (human T lymhotropic virus III$_B$) with immobilized trypsin 10 ml of an immunoglobulin-G-containing solution prepared in the same way as in Example 1 were mixed with 1 ml immobilized trypsin and 0.5 ml of a HTLV-III$_B$ suspension (R. C. Gallo et al., Science 224: 500–503, 1984) and treated under sterile conditions at 37° C. by stirring. Samples were taken at the beginning and after various time intervals and the virus activity was determined. The determination of the virus activity "Infectious Units/0.5 ml" was effected according to the technique indicated in the above document R. C. Gallo et al. As comparative solution for biologic activity assessment, a comparative solution as in Example 1 served.

The virus activities and the portion of IgG monomers in the comparative solution may be taken from Table 3: after 48 h the virus activity had disappeared, the portion of IgG monomers had been preserved to the major extent.

EXAMPLE 4

Inactivation of vaccinia virus with soluble hydrolase 1 ml of an immunoglobulin-G-containing solution prepared as in Example 1 was mixed with 0.1 ml of a 7.5% hydrolase solution (trypsin pankreas protease, Merck Article 8367) and with 0.1 ml of a vaccinia virus suspension (Vaccinia virus, ATCC VR-862, virus strain Elstree, American Type Culture Collection) and treated under sterile conditions at 37° C. A comparative solution of 1 ml immunoglobulin solution, 0.1 ml hydrolase solution and 0.1 ml virus-free medium was prepared and treated in the same way as the virus-containing solution. Upon sampling at different points of time, the virus titer, the content of tetanus antibodies and the portion of IgG monomers were determined, as described. The results are summarized in Table 4. After 48 hours, the virus titer was less than 1 with a sufficient IgG monomer portion.

EXAMPLE 5

Inactivation of Sindbis virus with soluble hydrolase 1 ml of an immunoglobulin-G-containing solution prepared as in Example 1 was mixed with 0.1 ml of a 7.5% hydrolase solution (trypsin pankreas protease) and 0.1 ml of a Sindbis virus suspension (ATCC VR-68, virus strain Elstree, American Type Culture Collection) and treated under sterile conditions at 37° C. A comparative solution of 1 ml immunoglobulin solution, 0.1 ml hydrolase solution and 0.1 ml virus-free medium was prepared and treated in the same manner as the virus-containing solution. Upon sampling at different points of time, the virus titer, the content of tetanus antibodies and the portion of IgG monomers were determined, as described. The results may be taken from Table 5. After 48 hours, the virus titer was less than 1 with a sufficient portion of IgG monomers.

EXAMPLE 6

Inactivation of HTLV-III$_B$ with soluble hydrolase 1 ml of an immunoglobulin-G-containing solution prepared as in Example 1 was mixed with 0.1 ml of a 7.5% hydrolase solution (trypsin pankreas protease) and 0.1 ml of a HTLV-III$_B$ virus suspension (R. C. Gallo et al.) and treated under sterile conditions at 37° C. A comparative solution of 1 ml immunoglobulin solution, 0.1 ml hydrolase solution and 0.1 ml virus-free medium was prepared and treated in the same way as the virus-containing solution. Upon sampling at different points of time, the virus activity, the tetanus antibodies and the portion of IgG monomers were determined, as described. The results may be taken from Table 6. After 72 hours, the virus activity had disappeared with a sufficient portion of IgG monomers and a satisfactory content of antibodies.

While the preceding examples illustrate the results of inactivation attainable upon addition of special model viruses, no virus addition takes place in the production process. The separation of the inactivating enzyme, which constitutes a preferred embodiment, in this case is performed after the stirring step at the temperatures indicated by selected measures, i.e., for instance, by filtration when using an immobilized enzyme and by adsorption at ion exchange or aluminum hydroxide when using a soluble enzyme.

TABLE 1

| Treatment with immobilized trypsin after | Virus Titer (log TCID$_{50}$/0.1 ml) vaccinia virus | Tetanus Antibodies (IU/ml) | IgG Monomers (%) |
|---|---|---|---|
| before beginning of treatment | 2.6 | 90 | 90.9 |
| 24 hours | 1.0 | 80 | 82.2 |
| 48 hours | less than 1.0 | 60 | 75.7 |
| 75 hours | less than 1.0 | 52 | 69.4 |

TABLE 2

| Treatment with immobilized trypsin after | Virus Titer (log TCID$_{50}$/0.1 ml) Sindbis virus | Tetanus Antibodies (IU/ml) | IgG Monomers (%) |
|---|---|---|---|
| before beginning of treatment | 4.5 | 90 | 90.9 |
| 24 hours | 3.1 | 80 | 82.2 |
| 48 hours | 2.5 | 60 | 75.7 |
| 75 hours | 1.9 | 52 | 69.4 |

TABLE 3

| Treatment with immobilized trypsin after | Virus activity (Infectious units/0.5 ml) HTLV-III$_B$ virus | IgG Monomers (%) |
|---|---|---|
| before beginning of treatment | 10$^6$ | 89.4 |
| 1 hour | 10$^4$ | 89.9 |
| 24 hours | 10$^0$ | 90.8 |
| 48 hours | 0 | 76.8 |
| 72 hours | 0 | 71.2 |

TABLE 4

| Treatment with soluble hydrolases after | Virus Titer (log TCID$_{50}$/0.1 ml) vaccinia virus | Tetanus Antibodies (IU/ml) | IgG Monomers (%) |
|---|---|---|---|
| before beginning of treatment | 2.1 | 90 | 82.9 |
| 5 hours | 1.2 | 90 | 83.5 |
| 24 hours | 1.0 | 70 | 66.1 |
| 48 hours | less than 1.0 | 65 | 52.5 |
| 72 hours | less than 1.0 | 55 | 41 |

TABLE 5

| Treatment with soluble hydrolases after | Virus Titer (log TCID$_{50}$/0.1 ml) Sindbis virus | Tetanus Antibodies (IU/ml) | IgG Monomers (%) |
| --- | --- | --- | --- |
| before beginning of treatment | 5.0 | 90 | 82.9 |
| 5 hours | 4.5 | 90 | 83.5 |
| 24 hours | 1.2 | 70 | 66.1 |
| 48 hours | less than 1.0 | 65 | 52.5 |
| 72 hours | less than 1.0 | 55 | 41 |

TABLE 6

| Treatment with soluble hydrolases after | Virus activity (Inf. Units/0.5 ml) HTLV-III$_B$ | Tetanus antibodies (IU/ml) | IgG Monomers (%) |
| --- | --- | --- | --- |
| before beginning of treatment | $10^5$ | 90 | 82.9 |
| 5 hours | $10^4$ | 90 | 83.5 |
| 24 hours | $10^2$ | 70 | 66.1 |
| 48 hours | $10^1$ | 65 | 52.5 |
| 72 hours | 0 | 55 | 41 |

What we claim is:

1. A method of inactivating reproductive filterable pathogens in an immunoglobulin-G-containing fraction which contains IgG monomers to be applied therapeutically or prophylactically, which method comprises the steps of preparing an aqueous solution of an immunoglobulin-G-containing fraction obtained from human blood, and treating said aqueous solution with neutral hydrolases at a temperature of 4° to 5° C. and at a pH of 5.5 to 9.5, thereby inactivating reproductive filterable pathogens, while preserving the IgG monomers to the major extent.

2. A method as set forth in claim 1, wherein said neutral hydrolase is comprised of at least one enzyme of the group of peptide hydrolases selected from the group consisting of trypsin, chymotrypsin, pepsin and carboxypeptidases.

3. A method as set forth in claim 2, which further comprises the steps of separating said at least one enzyme from said aqueous solution after inactivation so as to obtain a treated product, and further purifying and concentrating said treated product.

4. A method as set forth in claim 1, wherein said aqueous solution of said immunoglobulin-G-containing fraction is treated with a soluble hydrolase at a pH of 6.0 to 8.0.

5. A method as set forth in claim 1, wherein said aqueous solution of said immunoglobulin-G-containing fraction is treated with a neutral hydrolase bound to water insoluble carrier material at a pH of 5.5 to 8.5.

6. A method as set forth in claim 1, wherein treatment of said immunoglobulin-G-containing fraction is effected at elevated temperatures for a period of 1 hour to 36 days.

7. A method as set forth in claim 1, wherein said immunoglobulin-G-containing fraction has a protein concentration amounting to 0.1 to 18% by weight.

8. A method as set forth in claim 1, wherein said reproductive filterable pathogens are selected from the group consisting of hepatitis virus and HTLV-III/LAV virus (human T lymphotropic virus).

* * * * *

UNITED STATES PATENT AND TRADEMARK OFFICE
CERTIFICATE OF CORRECTION

PATENT NO. : 4,814,277
DATED : March 21, 1989
INVENTOR(S) : Johann EIBL and Yendra LINNAU It is certified that error appears in the above-identified patent and that said Letters Patent is hereby corrected as shown below:

Column 1, line 68, "activated" should read --inactivated--.
Column 2, line 67, "activation" should read --inactivation--.
Column 3, line 13, "precipitates" should read --precipitate--.
Column 4, at the end of line 30 there should be a period.
Column 4, line 34, "Ml" should read --ml--.
Column 4, line 49, "lymhotropic" should read --lymphotropic--.
Column 4, at the end of line 50 there should be a period.
Column 5, at the end of line 23 there should be a period.
Column 6, line 27, "exchange" should read --exchangers--.
Column 7, line 35, "5°" should read --50°--.
Column 8, line 36, "temperatures" should read --temperature--.

Signed and Sealed this

Twenty-third Day of October, 1990

Attest:

HARRY F. MANBECK, JR.

*Attesting Officer*     *Commissioner of Patents and Trademarks*